United States Patent [19]

Yokota

[11] 4,292,026
[45] Sep. 29, 1981

[54] ARTICULATOR

[76] Inventor: Seizo Yokota, 2nd Floor, Konoike Bldg., 14-45, Daimyo 1-chome, Chuo-ku, City of Fukuoka, Fukuoka Prefecture, Japan

[21] Appl. No.: 113,130

[22] Filed: Jan. 17, 1980

[30] Foreign Application Priority Data

Mar. 27, 1979 [JP] Japan ................................. 54-37489

[51] Int. Cl.³ ............................................ A61C 19/04
[52] U.S. Cl. ........................................ 433/69; 433/58
[58] Field of Search ....................... 433/68, 69, 71, 76, 433/54, 55, 56, 58

[56] References Cited

U.S. PATENT DOCUMENTS

| | | | |
|---|---|---|---|
| 1,989,367 | 1/1935 | Keeney | 433/58 |
| 3,452,439 | 7/1969 | Lee | 433/55 |
| 3,577,639 | 5/1971 | Lee | 433/69 |
| 4,026,024 | 5/1977 | Tradowsky | 433/68 |
| 4,111,085 | 9/1978 | Johnson | 83/801 |
| 4,204,326 | 5/1980 | Dimeff | 433/71 |

FOREIGN PATENT DOCUMENTS 48-37994  4/1973  Japan ................................. 433/68

*Primary Examiner*—Gene Mancene
*Assistant Examiner*—John J. Wilson
*Attorney, Agent, or Firm*—Wenderoth, Lind & Ponack

[57] ABSTRACT

An articulator for observing occlusion, in which the movement of the mandible with respect to the maxillary is transmitted exactly to a mandibular cast so as to cause an identical movement of the latter, and which can reproduce repeatedly the movement as it was at a desired time by tracing the condyle paths which are automatically formed in solid material by cutting tools mounted on members connected to the mandibular cast.

7 Claims, 11 Drawing Figures

ARTICULATOR

BACKGROUND OF THE INVENTION

This invention relates to an articulator in which the movement of the row of teeth of a human mandible with respect to the row of teeth on a maxillary is transmitted to a mandibular cast so as to cause a movement of the latter identical with the movement of the former and in which the identical movement can be repeatedly reproduced.

In dentistry, it is necessary to observe the state of occlusion of molars in motion in an intraoral cavity. However it is extremely difficult to make an accurate observation of the state of occlusion. For this observation an articulator is usually used. Conventional articulators first make a recording of a portion of the condyle paths, and then form the corresponding condyle paths indirectly on the articulator based on the recorded condyle paths. This operation is very difficult and requires a lot of time. Further more, as the glenoid fossa is concave, the condyle paths must also be formed by curved lines. However, heretofore, the paths have been formed by straight lines and angles, since it is difficult to form the condyle paths by curved lines.

Japanese Laid Open Patent Application No. 37,944/1973, which is an application of the present Applicant, provided an articulator which partly solves the above problem. However in this articulator all of the members of the articulator are suspended by suspending strings. Accordingly the row of teeth on the maxillary is easily moved, since the entire weight of the apparatus can swing on the strings, so that the condyle paths cannot be formed very exactly making it difficult to reproduce the movement exactly. Moreover, because most of the weight of the articulator driven by the mandible is supported by the mandible, so that natural movement is made difficult, thus making accurate reproduction of the movement difficult.

It is an object of the invention to provide an articulator for observing the occlusion, in which the movement of the row of teeth on the mandible with respect to the row of teeth on the maxillary in the intraoral cavity is accurately and directly transmitted to a mandibular cast so as to cause identical movement in the latter, and which can reproduce repeatedly the movement as it was at a desired time.

It is another object of the invention to provide an articulator which can be easily operated and which requires only a small force from the mandible of the patient.

The present invention is an articulator for observing the occlusion between a mandible and a maxillary, which comprises a frame, a first adjustable bite fork mounted on the frame for holding and positioning the maxillary, a second adjustable bite fork for holding the mandible, a mandibular cast adjustably mounted on the frame, a maxillary opposed to the mandibular cast, a link means for transmitting the exact movement of the mandible to the mandibular cast, and machining means which grinds solid material disposed on the frame and which is rigidly connected to the mandibular cast. When all the possible movements of the mandible are brought about, condyle paths are formed in the solid material. Every possible movement of the mandible is reproduced in the movement of the mandibular cast by tracing the formed condyle paths.

The link means comprises a beam fixed to the frame, two movable plates facing each other, three parallel rods which are connected to the plates at the ends thereof by means of ball joints, and positioned at the apexes of an isosceles triangle with the rods being parallel to the beam, two first arm plates which are rotatably mounted on two of the three horizontally parallel rods at one of their respective ends, and which are slidable on the two rods in the longitudinal direction, and two second arm plates which are mounted on the beam at one of their ends and are prevented from sliding on the beam in the longitudinal direction with other ends of each one of the first arm plates and second arm plates being rotatably connected to each other. One of the facing plates is connected to the second adjustable bite fork, and the other of the facing plates is connected to the mandibular cast.

According to an embodiment of the invention, the link means is enclosed in a box disposed on the lower portion of the frame.

The weight of the mandibular cast, the machining means and the movable members of the link means is balanced by springs so they are movable by small force.

The machining means are preferably vertically disposed burrs driven by a motor. The positional relationship of the mandibular cast with respect to the tip of the burrs is the same as that of the mandible with respect to the condyle points. The solid material is preferably made of plaster particles bonded with polymers and has a low contractibility and of high machinability.

As above described, the most outstanding feature of the articulator of the present invention is that the mandibular movements of the patient form the condyle paths i.e. the curvature of the functional glenoid fossa, directly. Consequently, it is not necessary to measure the terminal hinge or various condyle angles. The operation is very simple and is completed in a short time. Above all the exact mandibular movement of the patient can be reproduced.

BRIEF DESCRIPTION OF THE DRAWINGS

The above brief description, as well as further objects, features and advantages of the present invention, will be more fully understood by reference to the following detailed description of the presently preferred, but nonetheless illustrative, embodiment in accordance with the present invention when taken in conjunction with the accompanying drawings, wherein.

DESCRIPTION OF THE PREFERRED EMBODIMENT

Figure 1:
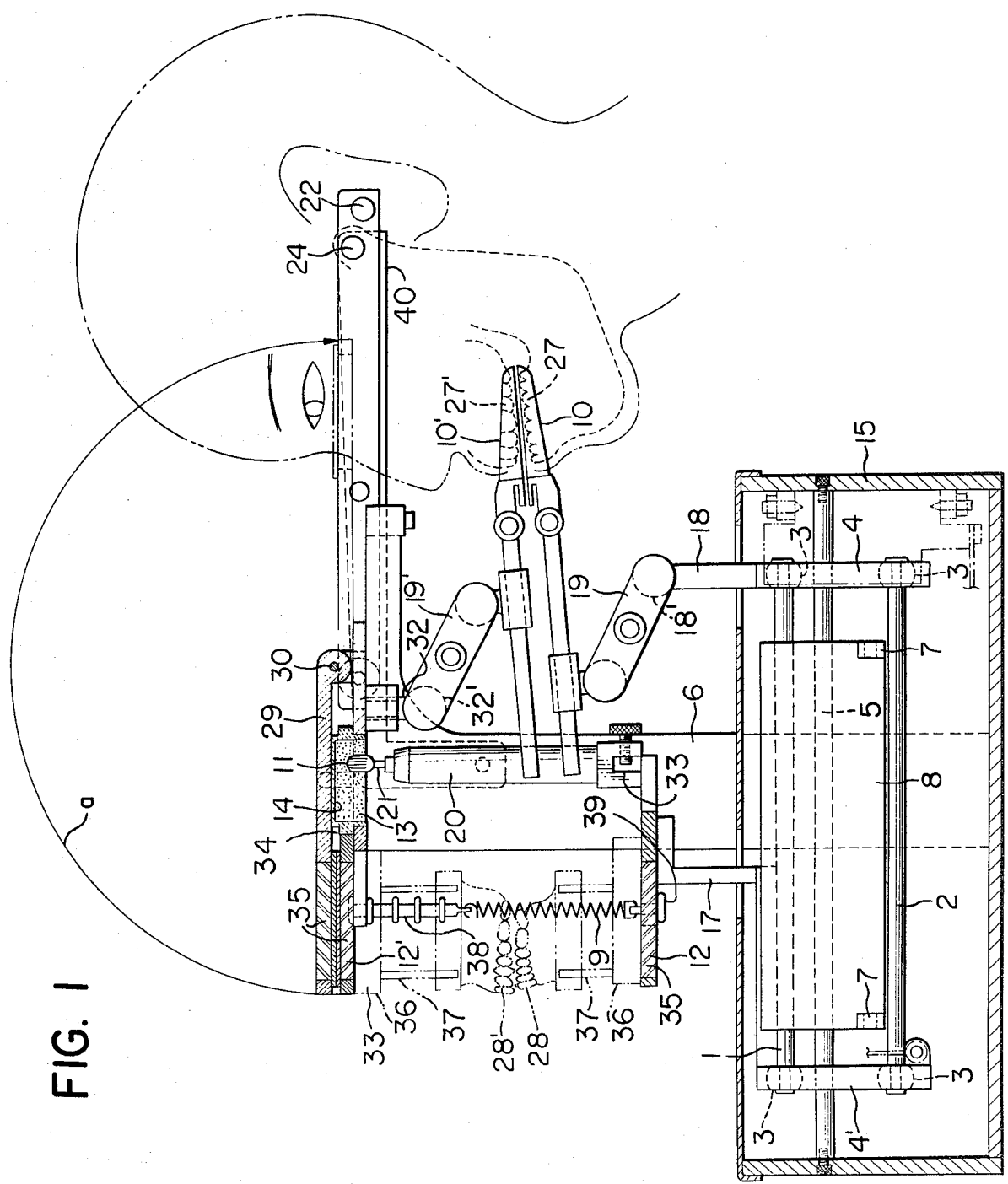
FIG. 1 is a side view partly in section of the articulator according to the present invention.
Figure 2:
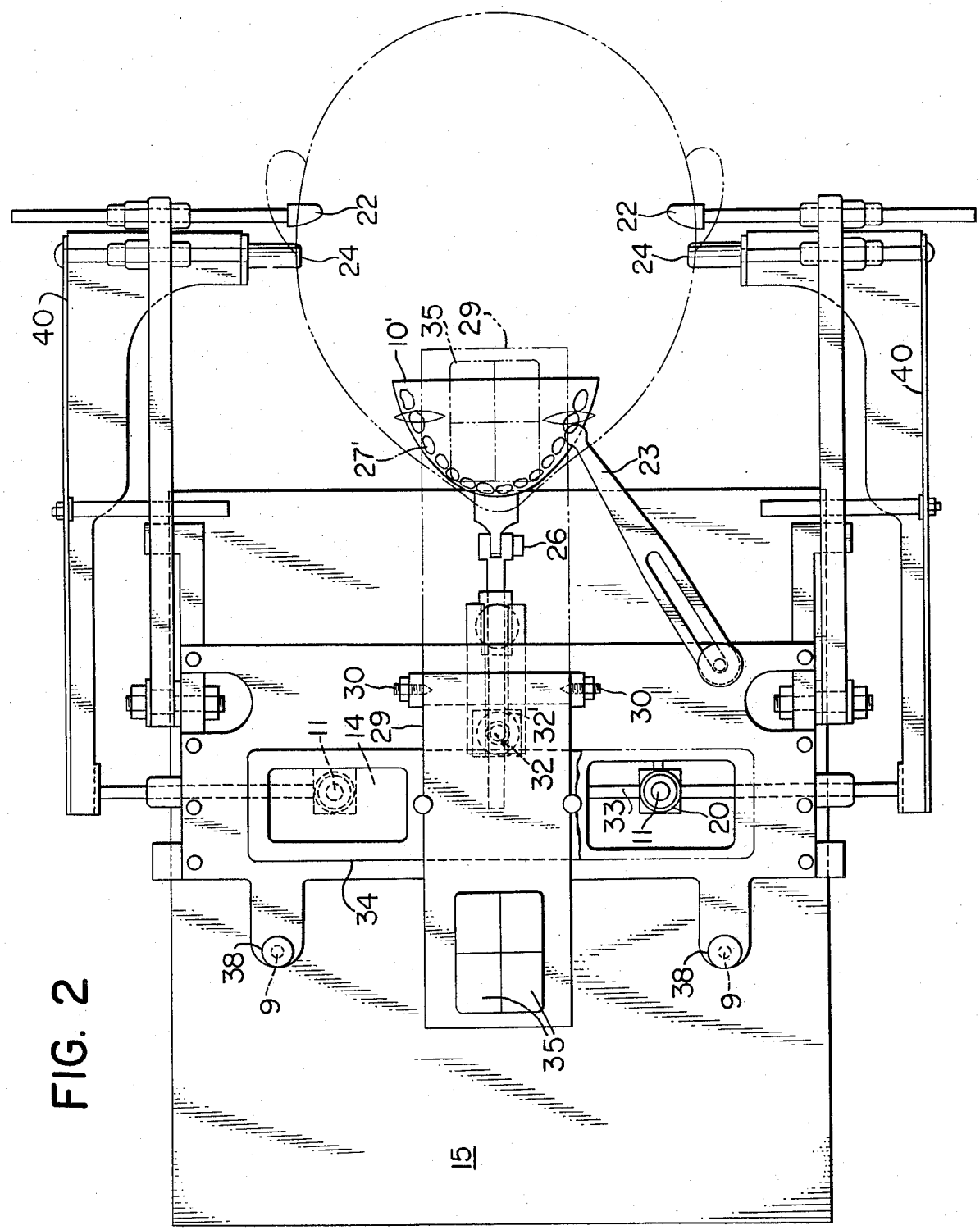
FIG. 2 is a plan view of the articulator shown in FIG. 1.
Figure 3:
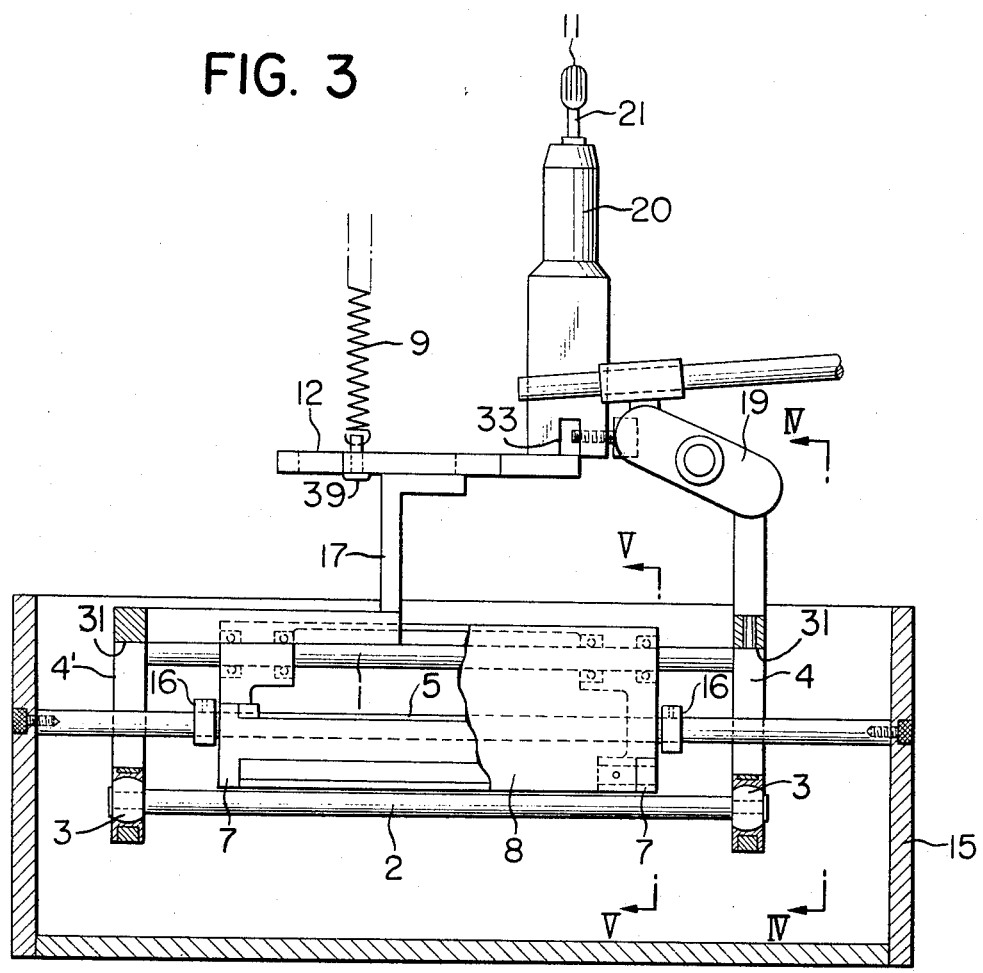
FIG. 3 is a side view, partly in section, showing the lower part of the articulator shown in FIG. 1.
Figure 4:
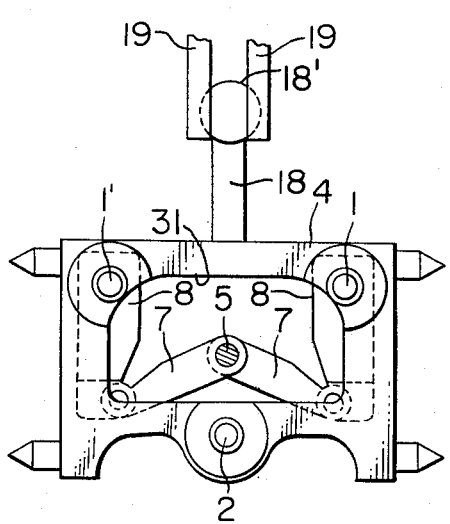
FIG. 4 is a sectional view of FIG. 3 along the line IV—IV.
Figure 5:
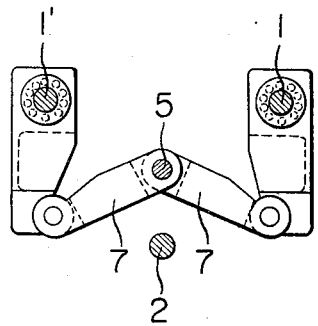
FIG. 5 is a sectional view of FIG. 3 along the line V—V.

Referring now to the drawings, in a box 15, mounted on the lower part of a frame 6, are housed two horizontally parallelly disposed upper rods 1 and 1' and a lower rod 2 parallelly disposed under the rods 1 and 1'. These three rods are at the apexes of an isosceles triangle, and each of the rods has the same length. To both ends of the rods 1, 1' and 2, two movable parallel plates 4 and 4' are connected by means of ball joints 3. A beam 5, which is parallel with the rods 1, 1' and 2 and lies approximately in the center of the triangle composed of the rods 1, 1' and 2, is fixed to the end walls of the box 15 at the ends thereof by fastener means such as screws. The upper rods 1, 1' and are connected to the beam 5 through links composed of upper arm plates 8 and lower arm plates 7 which are rotatably connected to each other. Longitudinal movements of the lower arm plates 7 with respect to the beam 5 are prevented by means of stops 16 fixed to the beam, while the upper rods 1 and 1' are slidable with respect to the lower arm plates 8. Movable parallel plates 4 and 4' each have, as shown in FIG. 4, a square shape with a large central opening 31 therein, and ball joints 3 are respectively provided at both corner ends of the upper side and the middle of the lower side 4 so that parallel rods 1, 1' and 2 are respectively journaled therein, parallel plates 4 and 4' being held in a parallel relationship with each other. Beam 5 extends through the openings 31 so as not to disturb the movement of plates 4 and 4'. As shown in FIGS. 3 and 5, upper arm plates 8 are slidably mounted on rods 1 and 1', respectively, and at their lower ends, the base ends of lower arm plates 7 being pivotally mounted on mounting beam 5. The assembly of the rods 1, 1' and 2, plates 4 and 4' and arm plates 7 and 8 is suspended by a pair of springs 9 and 9' from the frame 6 through a connecting bracket 17 connected to plate 4', so that the assembly can be moved by a small force. An upright arm 18 fixed to the middle of the other plate 4 extends upwards through the top of the box 15, and at a spherical portion 18' at the upper end of the arm 18 is provided an adjustable fitting 19, on an end of which a bite fork 10 for the row of teeth on the middle of the other plate is disposed. A bite fork 10' for the row of teeth on the maxillary and which faces the bite fork 10, is mounted on the frame 6 by an adjustable fitting 19' pivoted on a spherical portion 32' on the lower end of a downwardly directed arm 32. On the bracket 17 are disposed a pair of electric motors 20 adjustably mounted on guides 33 on bracket 17, on the output shafts 21 of which cutting tools 11 such as burrs are provided. The frame 6 has recesses 14 in positions corresponding to condyles of the mandibular and maxillary casts which will be explained later. The recesses 14 are filled with a solid material 13 which can be very easily tooled and can be cured very quickly by a curing agent. The material 13 is, for example, a solid made of plaster particles bonded with rapidly curable polymers and has a low contractibility and high machinability. A support member 12 for the mandibular cast 28 which is a model of a mandible is fixed to the bracket 17, while a support member 12' for the maxillary cast 28' which is a model of a maxillary is fixed to the frame 6. As described later, the position of the maxillary cast 28'0 is in an identical relationship to the cutting tools 11 as the relationship of the position of the human maxillary with respect to condyle points. On the frame 6 there are provided adjustable rod members 22 and 23 which can be set to correspond to the ear points and eye point respectively so that the position of the head of the patient is fixed. Members 24 as the relationship of the position of the frame 6 by pivots 30 and can be rotated through 180° as indicated by arrow a from the position shown in FIG. 1 to the position shown by dotted lines. The plate 29 is used to set the position of the maxillary cast 28' as described are mounted on beam members 40 so as to be movable against the patient's condyle points. A plate 29 is pivoted on the later. A box 34 having the recesses 14 therein is positioned on frame 6 from above. Plate-shaped permanent magnets 35 are provided in both plate 29 and frame 6. Adjustable holders 36 are provided to secure mandular casts to the apparatus as disclosed in U.S. Pat. No. 4,163,320, and they have claws 37 for supporting the mandular casts. Upper supports 38 are secured to frame 6 and lower supports 39 are secured to plate 12 for supporting the springs 9. Therefore, with the rows of the teeth 27 and 27' biting bite forks 10 and 10', as shown in FIG. 2, the tips of rod members 22 and the free end of rod member 23 correspond respectively to ear points and an eye point so that the plane defined by these points and the articulator are in parallel with each other. Fixing screws 25 and 26 are provided to fix the position of bite forks 10 and 10'.

The operation of the articulator will now be described.

The head of the patient is positioned and the members 24 are shifted by shifting beam members 40 so they come into contact with the condoyles of the patient. Then the position of the head is established by adjusting the rod members 22 and 23. Then the bite forks 10 and 10' are positioned between the rows 27 and 27' of the teeth which are in the occluded position, and fixed in this position. After setting the position of the bite forks 10 and 10', the head is withdrawn, and the plate 29 is pivoted through 180° from the position shown in FIG. 1 to the position shown by a dotted line in the same drawing. The upper surface of the plate 29 in the former position, is then in the same plane as the lower surface of the support member 12'. The maxillary cast 28' mounted on an adjustable holder 36 having a magnetic attaching means, is then magnetically attached to plate 29 and the holder 36 is adjusted until the maxillary cast 28' is brought into the position in which the maxillary cast 28' bites into the bite fork 10'; that is, the maxillary cast 28' is positioned in the same position as the maxillary of the patient. The adjustable holder 36 and the maxillary cast 28' are then removed from the plate 29 and attached to the support member 12'. According the vertical distance between the maxillary cast 28' and the base surface (which is the lower surface of the support member 12' and the lower surface of the plate 29 in the rotated position) is the same as that between the maxillary of the patient and the base surface. The motors 20 are mounted in positions such that the horizontal distance between the maxillary cast 28' and the cutting tools 11 is also as the same as the distance between the maxillary of the patient and the condyle points members 24. Accordingly the positional relationship between the maxillary cast 28' and the cutting tools 11 is the same as that between the maxillary of the patient and the condyle points. The mandibular cast 28 is set in the position opposed to the maxillary cast 28'.

Then the head of the patient is set in the initial position by using the rod members 22 and 23, and the mandible and the maxillary are occluded again.

When the rows 27 and 27' of teeth on the mandible and maxillary respectively occlude each other with the bite forks 10 and 10' therebetween, and the mandible is moved upwards, downwards, rightward and leftward and rotated with respect to the maxillary while the tools 11 are rotated by a motor, the mandibular cast 28 moves in the same manner as the mandible. That is to say, the mandibular cast 28 is moved forward and rearward as the mandible moves forward and rearward, since the rods 1, 1' and 2 and the plates 4 and 4' can slide along the beam 5. Further, when the mandible tilts in any direction, the mandibular cast 28 tilts the same way.

Figure 6:
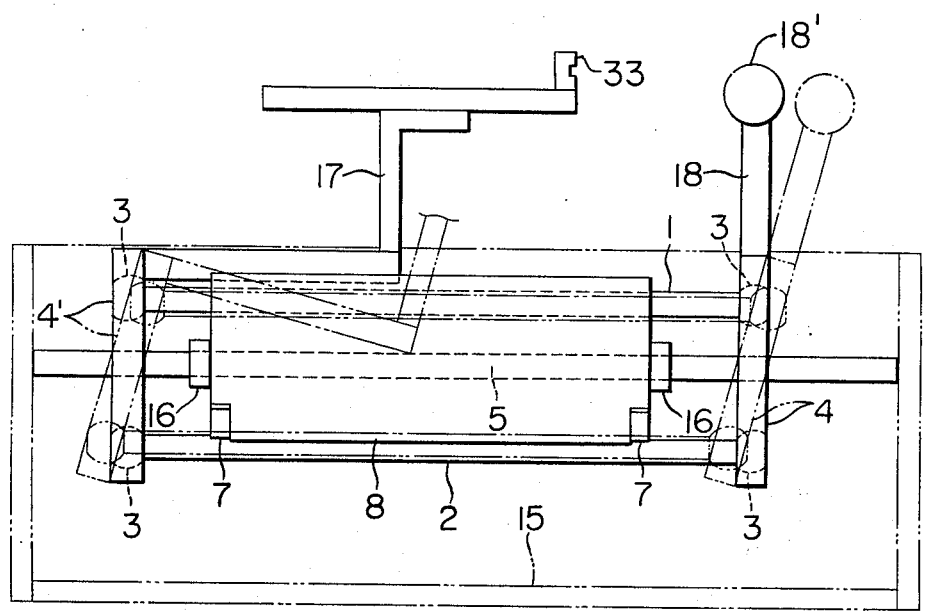
FIG. 6 is a sectional view similar to FIG. 3, showing the operation of the articulator.
Figure 7:
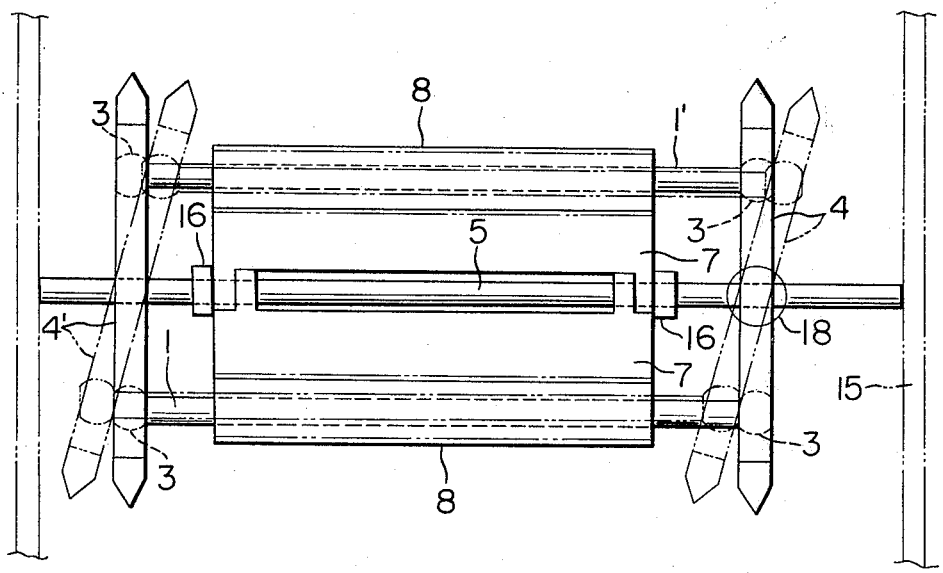
FIG. 7 is a plan view of the structure as shown in FIG. 6.

In FIG. 6, the manner of transmitting the tilting movement of the mandible is shown by the dot-dash line positions of the parts and the manner of transmitting the rotating movement of the mandible is shown in FIG. 7. As the operations shown in these drawings can be easily understood from the drawings themselves, further detailed explanations are omitted.

Figure 8:
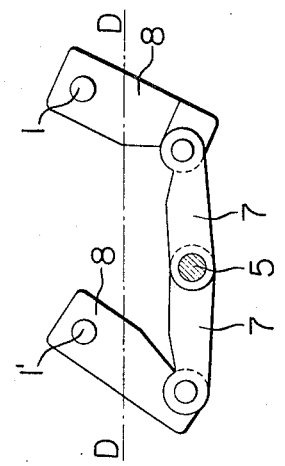
FIGS. 8 to 11 are sectional views similar to FIG. 5 showing the operation of the linkages.
Figure 9:
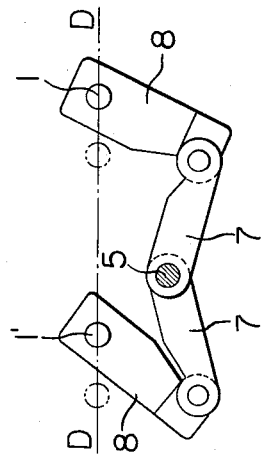
Figure 10:
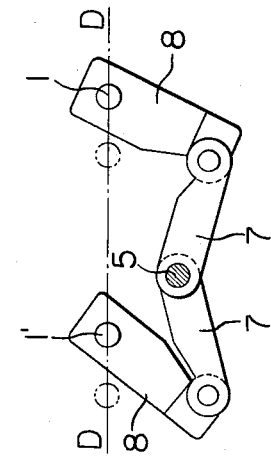
Figure 11:
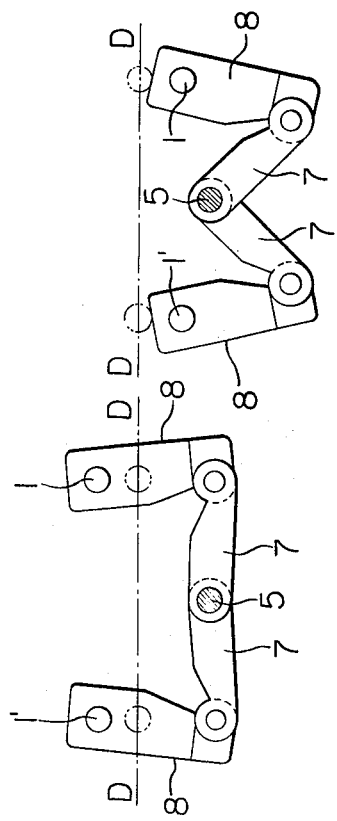

In FIGS. 8 to 11, the operations of the arm plates 7 and 8 to transmit the movement of the plate 4 to the plate 4' are shown. The dot-dash circles on line DD are the initial or normal positions of the rods 1, 1'. In FIG. 8 the plate 4 is moved upward from the normal position, and in FIG. 9 the plate 4 is moved downward. In FIG. 10 the plate 4 is moved to rightward and in FIG. 11 the plate 4 is moved rightward and upward. These drawings show that the plate 4' moves smoothly in accordance with the movement of the plate 4.

Accordingly the movement of the mandible in any direction with respect to the maxillary is transmitted to the mandibular cast 28 causing the same movement of the mandibular cast 28 with resepct to the maxillary cast 28'. Such movement of the mandibular cast 28 causes the cutting tools 11 move in the material 13 in the recesses 14. Accordingly the material 13 in the region in which the cutting tools 11 have moved is removed. The concave surfaces produced in the material 13 by this grinding simulate the total curvature of the functional glenoid fossa, from which the exact movements of the mandible can be reproduced.

When the movement of the mandibular cast 28 is desired to be reproduced, the mandibular cast 28 is moved by hand without rotating the motor 20. The cutting tools 11 are allowed to move only in the portions where the material 13 has been removed. Accordingly the mandibular cast 28 also is caused to move only in the restricted range which is determined by the range of the movement of the cutting tools 11. Thus the mandibular cast 28 will move in the same range with respect to the maxillary cast 28' as the range in which the mandible moves with respect to the maxillary.

It will now be apparent that, according to the articulator of this invention, the movement of the mandible with respect to the maxillary is transmitted exactly to the mandible cast so as to cause identical movement in the latter, and the movement can be reproduced repeatedly as it was at the desired time.

As will be readily apparent to those skilled in the art, the present invention may be produced in other specific forms without departing from its spirit or essential characteristics. The present embodiment is, therefore, to be considered as illustrative and not restrictive, the scope of the invention being indicated by the claims rather than by the foregoing description, and all changes which come within the meaning and range of equivalents of the claims are therefore intended to be embraced therein.

What is claimed is:

1. An articulator for reproducing the occlusion of a mandible and a maxillary of a patient, said articulator comprising:
   a fixed frame;
   a material holding means on said frame for holding a solid machinable material;
   a maxillary cast holding means removably mounted in a fixed position on said frame;
   a first bite fork adjustably mounted on said frame for holding and positioning the maxillary relative to said fixed frame;
   a second bite fork for holding the mandible, said second bite fork being opposed to said first bite fork;
   a link means on which said second bite fork is adjustably mounted for transmitting the movement of said mandible;
   a mandibular cast holding means on said link means and opposed to said maxillary cast holding means for holding a mandibular cast opposed to a maxillary cast on said maxillary cast holding means;
   machining means mounted on said link means for movement with said mandibular cast holding means; and
   a fixed beam attached to said frame on which a part of said link means is pivotally mounted and supporting part of the weight of said link means and spring means connected between said frame and said link means for supporting the remainder of the weight of said link means.

2. An articulator as claimed in claim 1 in which said link means comprises; two spaced plates facing each other, one of said facing plates being connected to said second bite fork and the other being connected to said mandibular cast holding means; three parallel rods extending between said facing plates and ball joints attaching the ends of said rods to said plates, said rods being positioned at the apexes of an isoceles triangle and said rods being parallel with said beam; two first arm plates each having one end rotatably mounted on a corresponding one of the three rods and being slidable on said rods in the longitudinal direction of the rods; and two second arm plates each having one end rotatably mounted on said beam and the other ends rotatably connected to a corresponding one of said first arm plates, and means for preventing said second arm plates from sliding on said beam in the longitudinal direction of said beam.

3. An articulator as claimed in claims 1 or 2 further comprising a box mounted on the lower portion of said frame, and said beam being mounted on said box, said link means being within said box.

4. An articulator as claimed in claims 1 or 2 in which said machining means comprise motors having vertically disposed burrs driven thereby.

5. An articulator as claimed in claim 4 in which the positional relationship of said mandibular cast holding means with respect to the tips of said burrs is the same as that of the mandible of the patient with respect to the condoyle points of the patient.

6. An articulator as claimed in claim 5 in which said frame further comprises a plate pivotally mounted thereon and pivotable to a position above the position of the maxillary of the patient with the downwardly facing surface thereof at the same level as the upper end of the maxillary cast holding means, and means on said plate for detachably mounting said maxillary cast holding means on said plate.

7. An articulator as claimed in claims 1 or 2 in which said machinable material is a material made of plaster particles bonded with polymers and has low contractibility, good machinability and is easily curable.

* * * * *